United States Patent [19]
Diaz et al.

[11] Patent Number: 5,891,441
[45] Date of Patent: Apr. 6, 1999

[54] CHEMICAL COMPOSITION AND METHOD FOR MORE RAPIDLY AIDING THE ABSORPTION, BINDING AN ELIMINATION OF UNDIGESTED FAT IN THE HUMAN BODY

[76] Inventors: Jose A. Diaz, 2950 Jackson Ave., Coconut Grove, Fla. 33133; Eduardo M. Naranjo, 14021 Cypress Ct., Coconut Grove, Fla. 33014

[21] Appl. No.: 135,933

[22] Filed: Aug. 18, 1998

Related U.S. Application Data

[63] Continuation-in-part of Ser. No. 888,848, Jul. 7, 1997, Pat. No. 5,795,576.

[60] Provisional application No. 60/021,299, Jul. 8, 1996.

[51] Int. Cl.$^6$ ........................ A61K 35/78; A61K 31/715; A61K 31/70
[52] U.S. Cl. ........................... 424/195.1; 514/54; 514/62
[58] Field of Search ........................... 424/195.1; 514/54, 514/62

[56] References Cited

U.S. PATENT DOCUMENTS

| | | |
|---|---|---|
| 3,533,940 | 10/1970 | Peniston et al. . |
| 3,879,376 | 4/1975 | Vanlerberghe et al. . |
| 3,953,608 | 4/1976 | Vanlerberghe et al. . |
| 4,034,121 | 7/1977 | Dunn et al. . |
| 4,119,619 | 10/1978 | Rogozhin et al. . |
| 4,223,023 | 9/1980 | Furda . |
| 4,758,861 | 7/1988 | Gori ........................................... 426/74 |
| 5,104,676 | 4/1992 | Mahmond et al. ...................... 426/590 |
| 5,462,742 | 10/1995 | Bogentoft et al. ....................... 424/439 |
| 5,612,039 | 3/1997 | Policappelli et al. ................. 424/195.1 |
| 5,690,981 | 11/1997 | Wantanabe et al. ..................... 426/531 |
| 5,795,576 | 8/1998 | Diaz et al. ........................... 424/195.1 |

*Primary Examiner*—Raymond Henley, III
*Attorney, Agent, or Firm*—Malloy & Malloy, P.A.

[57] ABSTRACT

A composition and method for the rapid elimination of fat from the human body, prior to digestion, is provided. A quantity of the chemical composition is intended to be ingested by humans, preferably with a glass of water prior to each meal, to aid in absorbing and binding fat, prior to its being digested, so that it may be rapidly eliminated from the human body, instead of stored as fat within the body. In a preferred embodiment the composition comprises at least one fibrous agent, and ideally, psyllium, in an amount of generally about 50% by weight of the composition, and an amount of glucosamine, preferably glucosamine HCL, at generally about 40% by weight of the composition, and amounts of glucomannan, apple pectin, and stearic acid forming the other generally about 10% by weight of the composition.

20 Claims, No Drawings

CHEMICAL COMPOSITION AND METHOD FOR MORE RAPIDLY AIDING THE ABSORPTION, BINDING AN ELIMINATION OF UNDIGESTED FAT IN THE HUMAN BODY

CLAIM OF PRIORITY

The present application is a continuation-in-part application of patent application Ser. No. 08/888,848, filed on Jul. 7, 1997, now U.S. Pat. No. 5,795,576 which claims priority under 35 U.S.C. Section 119(e) to a provisional patent application filed with the U.S. Patent Office on Jul. 8, 1996 and assigned Ser. No. 60/021,299, both of which are incorporated herein by reference.

BACKGROUND OF THE INVENTION

1. Field of the Invention

The present invention relates to a chemical composition and a method of treatment for accomplishing weight loss by a human ingesting the chemical composition in recommended dosages prior to eating a meal, thereby facilitating the absorption and binding of undigested fat to a fibrous agent for rapid elimination from the human body.

2. Description of the Related Art

In this day and age, many people's lifestyles have become less physically active. A natural result of a sedentary lifestyle is the tendency to gain weight, which is further compounded by the modern day tendency of many people to consume food which has a high fat content. Indeed, it is commonly thought that many people are now over-weight or at least moderately obese, and such individuals typically suffer from certain health problems associated with such conditions, at least at some later point in life, if not sooner than expected. Due to this trend, countless efforts have been made to help people control their weight. As a few examples, many have proclaimed to have won the "battle of the bulge" with a specific diet program or a particular exercise program. Others in the scientific arena formulated sugar substitutes and are pursuing fat substitutes as methods to reduce the caloric intake of an individual hopefully without, sacrificing the taste of otherwise highly fattening foods. While these efforts are generally capable of aiding many in their fight to lose weight and establish a healthier life style, many such attempts are generally ineffective or simply not practical. For example, some good meaning souls have tried in earnest to follow a particular diet plan but eventually, deviate from the plan because of lack of will-power in continue a given program for weeks or months at a time. Finally, some view sugar substitutes as being tasteless or carrying an intolerable health risk, given that some studies have linked them to carcinogens and/or the formation of brain tumors.

It has been appreciated in recent years that the fat content of foods which people eat are a major culprit behind human weight gain. For example, regardless of the type of fat present in a food product, fat has the highest caloric value per gram—about 9 calories per gram—of any food group. It is understood that the body tends to store fat for future use, rather than to utilize it immediately, and this factor helps lead to weight-gain. Unfortunately, fat also makes many food items more tasty—whether butter on bread, dressings on salads, sour cream on potatoes, or frosting on cake—and are therefore, difficult to eliminate entirely from one's diet. Thus, fat usually finds its way into the body. Once it does so, a healthy body automatically proceeds with the digestion process by the secretion of lipase, an enzyme that accelerates synthesis of fats, i.e., breaking down the fat molecule. The majority of all fats in foods are present in "triglyceride form", which the body seeks to break down by removing the glycerol molecule from the triglyceride and thereby, release the free fatty acids. Once this occurs, the body is well on its way to absorbing and storing the fat instead of utilizing it for energy.

From the foregoing, it will be understood that there remains an appreciable need in the art for a product and attendant safe and easy method of treatment which facilitates a person's efforts to lose weight. Any such product and method should be capable of aiding a person in accomplishing this goal without relying exclusively on a person's having sufficient will-power to maintain a strict diet and/or a rigorous exercise program. In addition, any such product and method should not interfere with the taste of foods. Ideally, any such product or method would permit a person to eat the foods that they most like, while not being as mindful about the amount of fats contained therein, and further, would prevent the body from absorbing the fat in such foods once they have been eaten. Any such product and method would ideally also aid the body in rapid elimination of the ingested fats in a safe, comfortable and natural manner. The present invention is designed to satisfy these and other needs which remain in the art and is believed to represent a significant advance in improving a person's health while facilitating weight loss by means of the rapid elimination of fat from the human body.

SUMMARY OF THE INVENTION

The present invention is directed to a novel chemical composition intended for ingestion by humans and a method which aids in weight loss. In particular, when the chemical composition of the present invention is ingested by a human prior to eating a meal, the composition acts to absorb and bind undigested fat to a fibrous agent so as to promote its rapid elimination from the human body. In accordance with this invention, the novel composition is moisture activated such that it remains inert and can be formed into capsules, preferably conveniently sized into predetermined doses for ingestion by a human, and will remain inert until it comes into contact with bodily secretions whether water of other liquid.

The chemical composition of the present invention preferably comprises a mixture of an amount of at least one fibrous agent, such as psyllium, at generally about forty to fifty percent (40% to 50%) by weight and most preferably between about 48% and 52% by weight, an amount of glucosamine, preferably glucosamine HCL at generally about or between 38% and 42% by weight, an amount of glucomannan generally between 5% and 6% by weight, an amount of fruit or vegetable derived pectin such as apple pectin generally about 2% by weight and an amount of stearic acid generally about or between 1% and 2% by weight of the composition. Upon contact with moisture, the composition begins to break down and becomes activated. Once activated, the composition acts quickly, usually within 30 seconds to seek and attach itself to undigested fats such as but not limited to oils and the like, and typically, within about 2 minutes will form a small mass of undigestible fibrous material. Additionally, a method for using the chemical composition is also described which comprises the steps of forming a single dose capsule of preferably about 500 milligrams, which contains the chemical composition, and having a human ingest at least two of said capsules preferably with about eight ounces of water about between fifteen to twenty minutes prior to a meal. While the size of the individual single dose may vary, one preferred embodiment of the present invention includes a human ingesting substantially about one thousand milligrams (1000 mg) of the composition before each meal.

A primary object of the present invention is to provide a chemical composition and method of treatment which serve as a convenient and effective means for reducing the quantity of fat digested and/or absorbed by the human body.

Another primary object of the present invention is to provide a chemical composition and method of treatment which seeks out, attaches and binds undigested fat, ingested by a human, to a fibrous agent, forming an undigestible mass which can easily and rapidly be eliminated from the human's body.

A feature of the chemical composition according to the present invention is that it is moisture activated and therefore is inert and can be formed into and stored as conveniently sized capsules until being ingested by a human and activated by coming in contact with bodily secretions whether water or other liquid.

Yet another object of the present invention is to provide a chemical composition which includes a blend of fibrous material for aiding the human body in rapid elimination of waste.

A feature of the present invention is that it can absorb at least five times its own weight in undigested fats.

These and other objects, features and advantages of the present invention will become readily apparent from the detailed description, which follows.

DETAILED DESCRIPTION OF THE PREFERRED EMBODIMENT

The present invention is directed towards a chemical composition and method of treatment utilizing the chemical composition which acts to absorb and bind undigested fat and rapidly eliminate the fat through the normal passage of waste from the human body prior to digestion or absorption of the fat. As a result of substantially reducing fat absorption, the present invention is also directed to a method of treatment which significantly aids weight loss in humans.

In the preferred embodiment, the chemical composition of the present invention primarily comprises at least one fibrous agent to act both as a vehicle for absorbing fat and, through substantial reduction in fat absorption, as a medium for allowing a significant reduction in weight gain in the human body. In the preferred embodiment, the fibrous agent used is psyllium and comprises at least about forty percent (40%) by weight of the composition, and ideally, between about 48% and 52% by weight of the composition. In one preferred embodiment, a single primary fibrous agent, such as psyllium, is used and comprises generally about 50% by weight of the composition. In other preferred embodiments, the composition of the present invention may comprise one or more other fibrous agents in addition to psyllium. For example, plantago ovata seed mucilage or the cover or husks of psyllium seeds may be utilized, which are very fibrous materials. Other fibrous agents in addition to psyllium may also be utilized, as described more fully below.

In addition to the fibrous agent psyllium, the composition of the present invention comprises glucosamine, a material derived from deacetylated shellfish shells or chitin. Chitin is known in the art as a naturally occurring polysaccharide—a polymer or long molecules consisting of sugar molecules strung together as shown by the general formula:

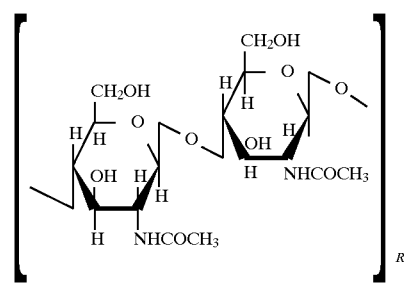

Chitin, which can be obtained from crab, lobster or shrimp shells by dissolving the shells' calcium carbonate and then removing protein fragments, leaving behind chitin as a white power, normally cycles through the environment, decomposing naturally into it hydrogen, carbon, nitrogen and oxygen building blocks. In one embodiment of the invention, glucosamine may be obtained from chitin by hydrolysis. Preferably, glucosamine salts and compounds derived from a monomer of chitin, namely, N-acetyl-D-glucosamine (GlcN Ac) which is represented by the general formula:

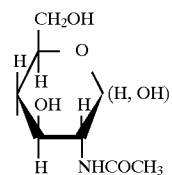

will be utilized such as, for example, glucosamine hydrochloride, acetylated glucosamines, and/or D-glucosamine. In a most preferred embodiment, glucosamine HCL and/or glucosamine hydrochloride will be utilized and will comprise generally about 38% to 42% by weight, and ideally about forty percent (40%) by weight of the composition. Glucosamine hydrochloride offers an additional side benefit in that it has been shown to be an efficacious alternative to corticosteroid treatment of enteritis and colonitis. It will be understood by those of ordinary skill in the art that as a derivative of chitosan, which has an ability to chelate various metal ions because of its hydroxy and amino groups act as electron donors, glucosamine HCL is an ion, or molecule having a negative charge, and which therefore, attracts and binds with certain molecules of food. In an alternative embodiment, a beta-alkylglycoside of N-acetyl-D-glucosamine may be utilized, which is represented by the general formula:

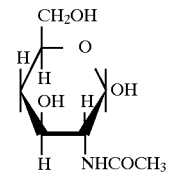

and is believed to effectively increase the ability of one's digestive tract to handle substantial quantities of lactose. In yet another alternative embodiment, the composition may comprise chitosan, instead of glucosamine. Chitosan is formed by adding the chitin, in its white powder form, to a concentrated sodium hydroxide solution which has been heated to above 135 degrees Celsius. This serves to remove one of chitin's side groups, i.e., to hydrolize the N-acetyl linkage, resulting in chitosan, which can be more readily dissolved. Chitosan, which is represented by the general formula:

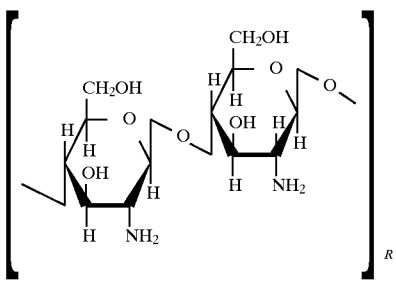

also has the ability to act as a coagulant, i.e., to attract and bind with certain molecules such as amino acids and proteins.

In the preferred embodiment of the present invention, the chemical composition comprises, in addition to psyllium and glucosamine HCL, a quantity of glucomannan—also known as Konjak or Konjac Root—which serves the purposes of providing lubrication and as well as providing an additional fibrous agent to the composition. Ideally, glucomannan comprises generally 5% and 6% and ideally 6% by weight of the composition. In addition, the chemical composition further comprises a pectin derived from fruits or succulent vegetables which serves the purpose of providing an additional fibrous agent to the composition. Most preferably, an apple pectin is used to form the composition which ideally, comprises generally about 2% by weight of the composition. Finally, in the preferred embodiment, the chemical composition also comprises a saturated fatty acid such as stearic acid, which serves the purpose of facilitating the processing and handling of a capsule containing the composition by permitting it to be smooth. Ideally, stearic acid comprises generally about 1% by weight of the composition.

In the preferred embodiment, the psyllium, glucosamine HCL, glucomannan, apple pectin and stearic acid are mixed together in powder form, although a granular form might also be suitable, and result in a mixture which is inert until it comes into contact with water, or other liquids such as is produced by the human body during digestion. Thus, in a most preferred embodiment, the present invention can be formed into capsules to facilitate ingestion, as well as packaging and storage. Additionally, the material used to form the encasement of the capsule will be inert when dry and upon coming into contact with water or other liquid will break down and permit both the release and subsequent activation of the chemical composition. Capsules also have the advantage of dissolving in a shorter period of time, thereby exposing the chemical composition to ingested fat in a shorter amount of time after ingestion. Alternatively, single doses of the composition could be formed into pills which would require ingestion by humans at a time which is a longer period before meals are consumed. If desired, the capsules containing the chemical composition according to the present invention may be packaged into bottles or like containers having a capacity for 50, 60, 75, 80, 100 or more capsules. Such packaging containers may also include a small, separately wrapped quantity of drying agent, such as a silica gel, in order to assume a dry storage environment desirable for preserving the inertness of the composition until use.

Ideally, the preferred embodiment of the composition of the present invention will be formed into capsules containing generally about 500 milligrams of the chemical composition in the following amounts: generally about 50% by weight of psyllium; generally about 40% by weight of glucosamine HCL; generally about 6% by weight of glucomannan; generally about 2% by weight of apple pectin; and generally about 1% to 2% by weight of stearic acid. It will be appreciated that a capsule containing about 500 milligrams has a size and overall dimension which is readily suited for being comfortably swallowed by a person in quantities corresponding to recommended doses. However, the capsule could be formed to contain less or more of the chemical composition (with ratios of the composition similar to that disclosed therein), and thereby be somewhat larger or smaller, and still be adequate for ingestion by a person. Testing experiments with the above described chemical composition have demonstrated the ability of the chemical composition to absorb at least to 5 times its own weight in fat. For instance, in one experiment 70 milliliters of water was placed in an appropriately sized test tube along with 10 grams (10,000 mg) of wheat germ oil and 100 milligrams of lecithin, the latter used as a substitute to replicate the emulsifying effect of gastric fluids normally present in a person's stomach. This mixture was shaken vigorously for about 10 seconds. Next, 1 gram (1000 mg) of the chemical composition according to the present invention was added and again, the mixture was shaken vigorously for about 10 seconds. After several minutes, the mixture was observed as having approximately fifty (50%) percent of fat (oil layer) gone, i.e., fat was no longer visible but instead had become bound with the fibrous agent of the composition so as to form an undigestible mass.

The chemical composition of the present invention lends itself well to a method of more rapidly aiding human weight loss, with a rapid and natural expulsion of fat in the feces. In particular, the chemical composition of the present invention seeks out and binds with fat ingested by a human prior to its being absorbed into the body, and as has been explained, binds them to a fibrous agent so as to aid the person in feeling "full" and further, to permit rapid and natural elimination by the human body. The preferred method of the present invention comprises the steps of forming a capsule of generally about 500 milligrams with the chemical composition and having the human ingest at least two of the 500 milligram capsules with generally about eight ounces of water about fifteen to twenty minutes before a meal. Ideally, the human will ingest two of the capsules before a meal, but may ingest up to about four or more of the capsules if the meal to be eaten is especially large and/or has a particularly high fat content. Upon being ingested by a human, each capsule begins to disintegrate and releases or otherwise facilitates activation of the chemical composition contained therein in typically, generally about thirty (30) minutes, and often less time. In a preferred form of the method there is an additional step of having the human ingest generally about eight ounces of water upon waking upon in the morning, and ideally, there is an additional step of having the human ingest about eight ounces of water between meals. When used substantially as directed, the chemical composition has been shown to decrease body weight and increase the percentage of fat in the feces.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed:

1. A chemical composition designed for the rapid elimination of fat from the human body prior to digestion, said composition comprising:

a) an amount of psyllium generally about 48% to 52% by weight of said composition, b) an amount glucosamine HCL generally about 38% to 42% by weight of said composition, c) an amount of glucomannan generally between 5% to 6% by weight of said composition, and d) an amount of fruit or vegetable derived pectin generally about of 1% to 2% by weight of said composition.

2. A chemical composition as resided in claim 1 wherein said fruit or vegetable based pectin comprises apple pectin.

3. A chemical composition as resided in claim 1 further comprising an amount of stearic acid generally between 1% and 2% by weight of said composition.

4. A chemical composition as resided in claim 3 wherein said fruit or vegetable based pectin comprises apple pectin.

5. A chemical composition as resided in claim 1 comprising a single dose defined by substantially 500 milligrams.

6. A chemical composition as resided in claim 5 wherein said dose comprises a capsule.

7. A chemical composition as resided in claim 5 wherein said dose comprises a pill.

8. A chemical composition designed to be ingested for the rapid elimination of fat from the human body, prior to digestion, said composition comprising:

a) an amount of psyllium of substantially about 50% by weight of said composition, b) an amount of glucosamine substantially about 40% by weight of said composition, c) an amount of glucomannan substantially about of 6% by weight of said composition, and d) an amount of apple pectin substantially above 2% by weight of said composition.

9. A chemical composition as resided in claim 8 comprising a single dose defined by a capsule of substantially 500 milligrams.

10. A chemical composition as resided in claim 9 further comprising an amount of stearic acid generally between 1% and 2% by weight of said composition.

11. A chemical composition designed for the rapid elimination of fat from the human body prior to digestion, said composition comprising:

a) an amount of psyllium generally about 50% by weight of said composition, b) an amount of chitosan generally about 40% by weight of said composition, c) an amount of glucomannan generally between 5% to 6% by weight of said composition, and d) an amount of apple pectin generally about 1% to 2% by weight of said composition.

12. A method of rapidly eliminating fat from the human body prior to digestion, said method comprising the steps of:

a) forming a single dose having a predetermined weight of a chemical composition comprising:

i) an amount of psyllium generally about 48% to 52% by weight of said composition, ii) an about of glucosamine HCL generally about 38% to 42% by weight of said composition, iii) an amount of glucomannan generally between 5% to 6% by weight of said composition, and iv) an amount of apple peccant generally about 1% to 2% by weight of said composition, b) having a human ingest a predetermined quantity of said doses prior to each meal.

13. A method as resided in claim 12 comprising having a human ingest an amount of at least substantially 1000 milligrams of said composition.

14. A method as resided in claim 12 comprising defining the single dose to be an amount substantially about 500 milligrams.

15. A method as resided in claim 14 comprising having the human ingested at least 2 doses of said composition before each meal.

16. A method as resided in claim 14 where said single dose is in capsule form.

17. A method as resided in claim 16 wherein said composition further comprises an amount stearic acid generally between 1% and 2% by weight of said composition.

18. A method of rapidly eliminating the undigested fat ingested by a human, said method comprising the steps of a) forming a chemical composition comprising:

i) an amount of psyllium substantially about 50% by weight of said composition, ii) an amount of glucosamine HCL substantially about 40% by weight of said composition, iii) an amount of glucomannan substantially about 6% by weight of said composition, iv) an amount of apple peccant substantially about 2% by weight of said composition, b) having a human ingested at least substantially about 1000 milligrams of said composition prior to each meal.

19. A method as resided in claim 18 further comprising forming a single dose of said chemical composition into a capsule of substantially about 500 milligrams.

20. A method as resided in claim 19 further comprising adding substantially between 1% and 2% by weight of stearic acid of said composition.

* * * * *